United States Patent [19]

Sielcken

[11] Patent Number: 5,679,831
[45] Date of Patent: Oct. 21, 1997

[54] PROCESS FOR THE PREPARATION OF AN ESTER

[75] Inventor: Otto E. Sielcken, Sittard, Netherlands

[73] Assignees: DSM N.V., Heerlen, Netherlands; E. I. Du Pont de Nemours and Company, Wilmington, Del.

[21] Appl. No.: 367,479

[22] Filed: Jan. 5, 1995

[30] Foreign Application Priority Data

Jan. 6, 1994 [BE] Belgium ............... 94 00009

[51] Int. Cl.⁶ ................ C07C 67/38; C07C 51/12; B01J 31/00
[52] U.S. Cl. ................ 560/204; 560/233; 560/239; 562/519; 502/162; 502/167
[58] Field of Search ............... 562/519; 502/162, 502/167; 560/204, 233, 239

[56] References Cited

U.S. PATENT DOCUMENTS

| | | | |
|---|---|---|---|
| 4,521,614 | 6/1985 | Jenck | 560/193 |
| 4,861,912 | 8/1989 | Drent et al. | 560/204 |
| 4,894,474 | 1/1990 | Maerkl et al. | 560/206 |
| 5,077,425 | 12/1991 | Burke | 558/353 |
| 5,194,631 | 3/1993 | Suto et al. | 549/71 |
| 5,292,700 | 3/1994 | Klusener et al. | 502/167 |
| 5,330,952 | 7/1994 | Drent | 502/162 |
| 5,340,787 | 8/1994 | Keijsper | 502/162 |
| 5,350,725 | 9/1994 | Van Doorn et al. | 502/162 |

FOREIGN PATENT DOCUMENTS

| | | | |
|---|---|---|---|
| A1-279477 | 8/1988 | European Pat. Off. | C07C 67/38 |
| A1-284170 | 9/1988 | European Pat. Off. | C07C 69/44 |
| A2-283194 | 9/1988 | European Pat. Off. | C07C 51/10 |
| A2-495547 | 7/1992 | European Pat. Off. | C07C 31/14 |
| 57-126425 | 8/1982 | Japan | C07B 29/00 |

*Primary Examiner*—Porfirio Nazario-Gonzalez
*Attorney, Agent, or Firm*—Cushman Darby & Cushman IP Group of Pillsbury Madison & Sutro,LLP

[57] ABSTRACT

Process for the preparation of a terminal ester by carbonylation of an internally unsaturated organic compound in the presence of an alcohol, carbon monoxide, palladium, an acid with a $pK_a$ of less than 2 (measured at 18° C. in an aqueous solution) and a bidentate organic phosphorus, antimony or arsenic ligand compound having a bridging group, wherein the bridging group comprises a bis(η-cyclopentadienyl) coordination group of a transition metal.

22 Claims, No Drawings

PROCESS FOR THE PREPARATION OF AN ESTER

FIELD OF THE INVENTION

The invention relates to a process for the preparation of a terminal ester by carbonylation of an internally unsaturated organic compound in the presence of an alcohol, carbon monoxide, palladium, an acid with a $pK_a$ of less than 2 (measured at 18° C. in an aqueous solution) and a bidentate organic phosphorus, antimony or arsenic ligand compound having a bridging group. Internally unsaturated compound means an unsaturated compound in which no terminal unsaturated bonds are present in the molecule.

BACKGROUND OF THE INVENTION

Such a process, wherein an internally unsaturated organic compound is carbonylated to the corresponding ester in the presence of a palladium containing catalyst, is described in EP-A-284170. In the process according to EP-A-284170 ethyl 3-pentenoate is carbonylated to terminal diethyl adipate with a selectivity of 70%. The selectivity to a certain compound, expressed in a percentage, is defined as 100*a/b in which "a" is the amount of starting compound that has been converted into a certain compound and "b" is the total amount of starting compound that has been converted. The carbonylation catalyst comprises palladium, 1,4-bis (diphenylphosphino)butane as the bidentate ligand compound and p-toluene sulphonic acid as the acid. A drawback of this process is that the selectivity towards the resulting terminal ester is low.

SUMMARY AND OBJECTS OF THE INVENTION

The object of the invention is to provide a process, in which the selectivity towards a terminal ester, for example diethyl adipate, is higher than is achieved in the process according to EP-A-284170.

This objective is accomplished in that the bridging group comprises a bis(η-cyclopentadienyl) coordination group of a transition metal.

It has been found that when the process according to the invention is applied to prepare an ester, the selectivity towards the terminal ester is higher than achieved with the process according to EP-A-284170. Furthermore higher reaction rates (mol substrate/mol Pd/hour) are possible with the process according to the invention compared to the process of EP-A-284170.

DETAILED DESCRIPTION OF THE INVENTION

The present process for preparing a terminal ester involves the carbonylation of an internally unsaturated organic compound in the presence of an alcohol, carbon monoxide, an acid having a $pK_a$ of less than 2 (measured at 18° C. in an aqueous solution) and a bidentate organic phosphorus, antimony, or arsenic ligand compound having a bridging group, wherein said bridging group comprises a bis(η-cyclopentadienyl) coordination group of a transition metal.

The bidentate ligand preferably comprises two phosphorus, antimony or arsenic atoms, which two atoms are directly or indirectly connected by the divalent bis(η-cyclopentadienyl) coordination group in which the ligand contains less than 40 carbon atoms. Apart from the bridging group, two organic groups, which preferably have 1–20 carbon atoms, are also bonded to each phosphorus, antimony and arsenic atom. Bis(η-cyclopentadienyl) coordination compounds and its derivatives are generally referred to as metallocene compounds.

The bidentate ligand compound more preferably has the following general formula:

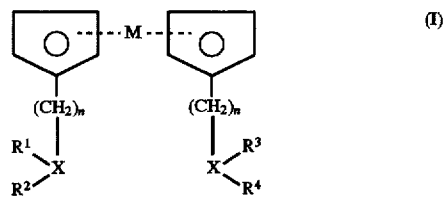

where n=0 or 1, X represents a phosphorus, antimony or arsenic atom, M represents a transition metal chosen from the group comprising Fe, Zr, Co, Cr, Ni, Ti, Ru and W, and $R^1$, $R^2$, $R^3$ and $R^4$ represent individually an organic group with 1–20 carbon atoms. The divalent bis(η-cyclopentadienyl) coordination compound is represented in formula (I) by the two pentadienyl groups, which groups are linked with each other via the transition metal M.

Of the four organic groups $R^1$, $R^2$, $R^3$ or $R^4$, preferably at least one, more preferably at least three and still more preferably all four is/are a $C_1$–$C_{20}$ (cyclo)alkyl or aralkyl group. It has been found that when the ligand compound contains one or more of these (cyclo)alkyl or aralkyl groups, the selectivity towards the linear ester increases. Examples of suitable (cyclo)alkyl or aralkyl groups are for instance the methyl, ethyl, propyl, isopropyl, butyl, isobutyl, tert-butyl, cyclopentyl, cyclohexyl, cycloheptyl, cyclooctyl, cyclodedecyl and benzyl groups. Besides these (cyclo)alkyl or aralkyl groups other organic groups may also be linked to the phosphorus, arsenic and antimony atoms. Examples of suitable other organic groups are aryl or aralkyl groups with 6–20 carbon atoms, for example phenyl, benzyl and naphthyl groups.

The cycloalkyl, aryl or aralkyl groups may optionally be substituted with $C_1$–$C_4$ alkyl groups, for example methyl, ethyl, n-propyl, isopropyl, n-butyl, isobutyl and tert-butyl. The alkyl, cycloalkyl, aralkyl or aryl groups may also be substituted with for example $C_1$–$C_4$ alkoxy, amine, halogenide groups, for example chlorine and bromine, and with other cycloalkyl and aryl groups such as defined above.

The cyclopentadienyl group of the metallocene compound may optionally be substituted with, for example, one or more aryl or alkyl groups or with other functional groups. Examples of these groups are $C_1$–$C_4$ alkyl groups, for example methyl, ethyl, propyl, isopropyl, butyl, isobutyl, tert-butyl, and carboxyl, hydroxyl, amine and halogenide groups, for example chloride and bromide. Other possible substituents are divalent organic groups with 1–20 carbon atoms, which groups may be used to immobilize the bidentate ligand on a carrier. One end of the divalent group may be bonded to the cyclopentadienyl group and the other end may be bonded to a carrier. Examples of possible divalent organic groups are $C_1$–$C_{20}$ alkylidene groups, for example methylene, ethylene, trimethylene, tetramethylene, pentamethylene, hexamethylene and icosamethylene. Examples of possible carriers are organic carriers for example polyethene, polystyrene, poly(styrene-co-diphenylbenzene) resin or inorganic carriers, for example silica, alumina and titanium oxide.

Preferably, Fe is used as transition metal in the metallocene compound (the bridging group being a ferrocene). An example of a method how to prepare a ligand compound which can be used in the process according to the invention is described in W. R. Cullen, F. W. B. Einstein, T. Jones, T.-J. Kim, Organometallics (1983), 2, 714.

Preferably, phosphorus ligands are used (wherein X in formula (1) is a phosphorus atom) because these ligands are more stable than the arsenic or antimony based ligands.

Preferably, n in formula (I) is equal to 0, the cyclopentadienyl group being directly bonded to X.

Examples of suitable bidentate phosphine ligand compounds used in the process according to the invention are 1,1'-bis(diphenylphosphino)ferrocene,
1,1'-bis(diisopropylphosphino)ferrocene,
1,1'-bis(diisobutylphosphino)ferrocene,
1,1'-bis(dipropylphosphino)ferrocene,
1,1'-bis(dicyclohexylphosphino)ferrocene,
1,1'-bis(isopropylcyclohexylphosphino)ferrocene,
1,1'-bis(ditert.butylphosphino)ferrocene,
1-(diisopropylphosphino)-1'-(phenylisopropylphosphino)ferrocene,
1,1'-bis(di-2-thiophenylphosphino)ferrocene,
1-(diphenylphosphino)-1'-(diisopropylphosphino)ferrocene and
1,1'-bis(isopropylphenylphosphino)ferrocene.

The palladium compound may be present in the reaction mixture as a heterogeneous palladium compound or as a homogeneous palladium compound. However, homogeneous systems are preferred. Since palladium in situ forms a complex with the bidentate ligand, the choice of the initial Pd compound is not critical. Examples of homogeneous palladium compounds are palladium salts of for instance nitric acid, sulphonic acid, alkane carboxylic acids with not more than 12 carbon atoms or hydrogen halogenides (for example HF, HCl, HBr, HI). Metallic palladium may also be used. Examples of such palladium compounds are Pd(II) acetate, $PdCl_2$, $PdBr_2$, $PdI_2$, $Na_2PdI_4$, $K_2PdI_4$, $Pd(NO_3)_2$ and bis(allylpalladium chloride). Another group of suitable palladium compounds are palladium complexes such as palladium acetylacetonate ($Pd(acetylacetonate)_2$), o-toluyl phosphine palladium, $PdCl_2(benzonitrile)_2$ and palladium (benzylidene acetone)$_2$. An example of a suitable heterogeneous palladium compound is palladium on an ion exchanger, such as an ion exchanger containing sulphonic acid groups.

The alcohol used in the process according to the invention preferably contains 1 to 20 carbon atoms, and more preferably 1 to 12 carbon atoms, and may contain more than one hydroxy group. The alcohol may be aliphatic, cycloaliphatic or aromatic. Examples of these last two groups of alcohols are cyclohexanol and phenol. Preferably alkanols are used. Suitable alkanols are for example methanol, ethanol, propanol, 2-propanol, butanol, 2-butanol, tert-butanol and pentanol. More preferably, alkanols with less than 5 carbon atoms are used. Most preferably, methanol and ethanol are used.

Suitable acids used in the process according to the invention are acids having a $pK_a$ of less than 2 (measured at 18° C. in an aqueous solution). Suitable acids are for example fluoro carboxylic acids, for example trifluoro acetic acid. Particularly suitable acids are $HClO_3$, $H_2SO_4$ or $RSO_3H$ in which R represents an—optionally substituted—hydrocarbon group. This hydrocarbon group (R) can be, for example, an alkyl, aryl, aralkyl or an alkaryl group with 1–30 and in particular 1–14 carbon atoms. The hydrocarbon group may, for example, be substituted with one or more halogen atoms, in particular with one or more fluorine atoms. Examples of suitable acids of formula $RSO_3H$ are 2-hydroxypropane-2-sulphonic acid, p-toluene-sulphonic acid, methane sulphonic acid and trifluoromethane sulphonic acid. The acid in accordance with the general formula $RSO_3H$ may optionally be an ion exchanger containing sulphonic acid groups, for example Amberlite 252 H and Amberlist 15 (Amberlite 252 and Amberlist 15 are brand names of Rohm and Haas). These ion exchangers are based on a hydrocarbon polymer, for instance polystyrene.

The process according to the invention can be carried out with application of the ratios mentioned below. However, these ratios are not critical and are only meant to provide an indication of how the process can be carried out. The process according to the invention may also be carried out outside the ranges mentioned, if so desired.

The molar ratio of the acid with a $pK_a$ of less than 2 to the bidentate ligand compound is preferably greater than 0.5.

The molar ratio of alcohol to internally unsaturated compound may preferably lie between approximately 1:1 and 20:1 and more preferably may be between 1:1 and 10:1.

The molar ratio of palladium to the internally unsaturated organic compound (substrate) is preferably between 1:10, 000 and 1:1.

The molar ratio of bidentate ligand compound to palladium is preferably between 0.5:1 and 10:1, and more preferably is between 1:1 and 5:1.

The temperature and pressure may be varied within wide limits. The temperature may lie between 50 and 200° C. and the pressure may lie between 2.5 and 10 MPa.

Besides carbon monoxide, inert gases such as nitrogen may be present. Small quantities of hydrogen can also be present. It is therefore possible to use, for example, technical carbon monoxide with 0.1–3 vol. % hydrogen.

The internally unsaturated organic compound (the substrate) preferably is a substituted or unsubstituted alkene with 4 to 30, in particular 4 to 20, and more particularly particular 4 to 10 carbon atoms. One or more unsaturated bonds may be present in the molecule. Preferably, these unsaturated bonds are not conjugated. Most preferably, only one unsaturated bond is present in the molecule, as for instance in 2-octene or 3-octene. It has been found in fact that for the eventual selectivity towards the terminal ester it makes little difference where the internally unsaturated bond is located. Examples of suitable internally unsaturated organic compounds are 2-butene, 2-pentene, 2-hexene, 3-hexene, 2-heptene, 3-heptene, 2-octene, 3-octene, 4-octene, 4-hexene amide, 2-pentenol, 2-butenol, 2-pentenol, 2-pentene nitrile, 3-pentene nitrile, 2-pentenoic methyl ester and 3-pentenoic methyl ester.

The process according to the invention may advantageously be used for the preparation of the terminal diester starting from an internally unsaturated carboxylic acid ester. More particularly, the process can be used to prepare dialkyl adipate starting from the internally unsaturated alkyl pentenoate and the corresponding alkanol. The alkyl pentenoate can be prepared from butadiene by the processes which are described for example in the above-mentioned EP-A-284170 and in EP-A-450577, U.S. Pat. No. 5,077,425, EP-A-301450 and U.S. Pat. No. 4,894,474 the complete disclosures of which are incorporated herein by reference. With these processes a mixture of alkyl pentenoates is prepared, which contains mainly alkyl 3-pentenoate (as a rule the mixture contains more than 50% alkyl 3-pentenoate). This mixture of alkyl pentenoates can be converted advantageously to the linear dialkyl adipate by means of the process according to the invention.

Suitable pentenoates are alkyl pentenoate, with 1 to 8 carbon atoms in the alkyl group. Examples of suitable alkyl groups and other suitable groups will correspond to the alkanols used in the carbonylation according to the invention as already described above. Preferably, the alkyl pentenoate is a methyl or ethyl pentenoate and the alkanol according to the invention is methanol or ethanol, respectively.

The content possible of hydroperoxide compounds should be kept as low as possible. These compounds may react with the bidentate ligand compound to form a catalytically inactive compound. The hydroperoxide compounds may form when the pentenoate ester is contacted with (small amounts) of oxygen. Therefore the contacting with oxygen should be avoided and/or the hydroperoxide compounds which may be present should be removed from the pentenoate ester (mixture) before the reaction. The removal of the hydroperoxide compounds may be for example performed by passing the hydroperoxide containing mixture over an ordinary activated alumina catalyst. The content of hydroperoxide compounds is preferably lower than 100 ppm and more preferably lower than 50 ppm.

The dialkyl adipate obtained by the process according to the invention can be readily converted to adipic acid by saponification of the ester group. The thus formed adipic acid may advantageously be applied as starting material for the preparation of, for example, nylon-6.6 or nylon-4.6.

The process can for example be carried out in the presence of a solvent. A suitable solvent is as a rule an organic solvent. Advantageously the unsaturated organic compound, the ester obtained and/or by-products of the process according to the invention may be used as solvent. Other suitable solvents are for instance ketones, e.g. acetophenon and cyclohexanon; ethers, e.g. diethyl ether, anisole and diphenyl ether; aromatic compounds, e.g. benzene, toluene and xylene; alkanes, e.g. hexane, heptane, cyclohexane, methyl cyclohexane and isooctane, and esters, e.g. methyl benzoate.

The invention will be elucidated by means of the following non-restrictive examples.

EXAMPLE I

A 50 ml Parr autoclave, made of Hastelloy C, was successively filled with 0.070 g (0.31 mmol) of Pd(II) acetate, 0.262 g (0.6 mmol) of 1,1'-bis (diisopropylphosphino)ferrocene, 0.59 g (3.1 mmol) of p-toluene sulphonic acid, 5.56 g (174 mmol) of methanol and 9.25 g of diphenyl ether. The autoclave was closed and purged three times with 4.0 MPa carbon monoxide. Next, under a pressure of 3.0 MPa CO and with stirring at a speed of 1250 rpm, 0.29 g nonane (internal standard for GC product analysis) and 7.80 g (68 mmole) of methyl 3-pentenoate were injected under pressure from an injection vessel into the autoclave. The reaction mixture was brought to a temperature of 130° C. at a CO pressure of 6.0 MPa. After 1 hour the reaction was stopped and the reaction products were analyzed by gas chromatography.

The conversion of the methyl 3-pentenoate amounted to 89.0% with a selectivity towards dimethyl adipate of 85.0%.

EXAMPLE II

In the same way as in example I a reaction was carried out, with the phosphine ligand replaced by 1-(diphenylphosphino)-1'-(diisopropylphosphino)ferrocene. The reaction was carried out with 0.017 g (0.07 mmol) of Pd(II) acetate, 0.120 g (0.2 mmol) of 1-(diisopropylphosphino)-1'-(diphenylphosphinoferrocene), 0.174 g (3.1 mmol) of p-toluene sulphonic acid, 5.35 g (167 mmol) of methanol and 8.91 g of diphenyl ether. Via an injection vessel 0.40 g of nonane and 7.04 g (62 mmol) of methyl 3-pentenoate were injected into the autoclave. The reaction was stopped after 1 hour. The conversion of methyl 3-pentenoate amounted to 76.0% with a selectivity towards dimethyl adipate of 78.0 mol%. The reaction rate was 668 mol of methyl 3-pentenoate converted per mol of palladium per hour.

EXAMPLE III

In the same way as in example I a reaction was carried out, with the phosphine ligand described there replaced by 1,1'-bis(isopropylphenylphosphino)ferrocene. The reaction was carried out with 0.026 g (0.12 mmol) of Pd(II) acetate, 0.58 g (0.12 mmol) of 1,1'-bis(isopropylphenyl)ferrocene, 0.330 g (1.7 mmol) of p-toluene sulphonic acid, 4.80 g (150 mmol) of methanol and 10.40 g of diphenyl ether. Via an injection vessel 0.770 g of nonane and 6.950 g (61 mmol) of methyl 3-pentenoate were injected into the autoclave. After 5 minutes of reaction the conversion of the methyl pentenoate amounted to 62.0% with a selectivity towards dimethyl adipate of 79.0 mol%. The reaction rate was 3700 mol of methyl 3-pentenoate converted per mol of palladium per hour.

EXAMPLE IV

In the same way as in example I a reaction was carried out with 0.007 g (0.031 mmol) of Pd(II) acetate, 0.015 g of 1,1'-bis(diisopropylphosphino)ferrocene, 0.128 g (0.7 mmol) of p-toluene sulphonic acid, 5.34 g (167 mmol) of methanol and 8.69 g of diphenyl ether. Via an injection vessel 0.691 g of nonane and 8.259 g (72 mmol) of methyl 3-pentenoate were injected into the autoclave. The reaction was stopped after 1 hour. The conversion of the methyl pentenoate amounted to 49% with a selectivity towards dimethyl adipate of 86 mol %. The reaction rate was 1200 mol of methyl 3-pentenoate ester converted per mol of palladium per hour.

EXAMPLE V

Example I was repeated at a reaction temperature of 115° C. After 1 hour the conversion of the methyl 3-pentenoate was 83%, with a selectivity of 84 mol % towards the dimethyl adipate.

EXAMPLE VI

Example I was repeated at a reaction temperature of 90° C. After 1 hour the conversion was 71%, with a selectivity of 84 mol % towards the dimethyl adipate.

EXAMPLE VII

Example V was repeated with the diphenyl ether replaced by 7.56 g of toluene. After 1 hour of reaction the conversion was 85%, with a selectivity of 84 mol % towards the dimethyl adipate.

EXAMPLE VIII

Example V was repeated with the p-toluene sulphonic acid replaced by 0.323 g (3.4 mmol) of methane sulphonic acid. After 1 hour the conversion was 81%, with a selectivity of 85 mol % towards the dimethyl adipate.

EXAMPLE IX

Example I was repeated with the diphenyl ether replaced by anisole. After 2 hours of reaction the conversion was 99%, with a selectivity of 83 mol % towards the dimethyl adipate.

EXAMPLE X

Example I was repeated with diglyme as solvent. After 1 hour of reaction the conversion was 89%, with a selectivity of 84 mol % towards the dimethyl adipate.

EXAMPLE XI

Example I was repeated, with the p-toluene sulphonic acid replaced by sulphuric acid. After 1 hour of reaction a conversion of 57% was reached, with a selectivity of 84 mol % towards dimethyl adipate.

The by-products obtained along with the dimethyl adipate were branched diesters in all examples (I–XI).

What I claim is:

1. A process for the preparation of a terminal ester by carbonylation of an internally unsaturated organic compound in the presence of an alcohol, carbon monoxide, palladium, an acid with a $pK^a$ of less than 2 (measured at 18° C. in an aqueous solution) and a bidentate organic phosphorus, antimony or arsenic ligand compound having a bridging group, wherein the bridging group comprises a bis(η-cyclopentadienyl) coordination group of a transition metal.

2. A process according to claim 1, wherein the bidentate ligand compound has the following general formula:

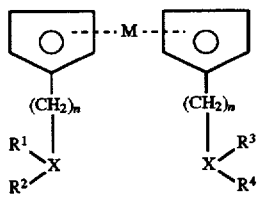

wherein n=0 or 1, X represents a phosphorus, antimony or arsenic atom, M represents a transition metal chosen from the group consisting of Fe, Zr, Co, Cr, Ni, Ti, Ru and W and $R^1$, $R^2$, $R^3$ and $R^4$ represent individually an organic group with 1–20 carbon atoms.

3. A process according to claim 2, wherein at least one of the groups $R^1$, $R^2$, $R^3$ and $R^4$ is a (cyclo)alkyl or aralkyl group.

4. A process according to claim 3, wherein $R^1$, $R^2$, $R^3$ and $R^4$ are $C_1$–$C_{20}$ (cyclo)alkyl or aralkyl groups.

5. A process according to any one of claims 1–4, wherein the transition metal is Fe.

6. A process according to any one of claims 1–4, wherein the bidentate ligand is a bidentate phosphine ligand.

7. A process according to any one of claims 1–4, wherein the internally unsaturated compound is a substituted or non-substituted alkene with 4 to 20 carbon atoms.

8. A process according to claim 1, wherein the bidentate ligand is a bidentate phosphine ligand selected from the group consisting of:

1,1'-bis(diphenylphosphino)ferrocene,
1,1'-bis(diisopropylphosphino)ferrocene,
1,1'-bis(diisobutylphosphino)ferrocene,
1,1'-bis(dipropylphosphino)ferrocene,
1,1'-bis(dicyclohexylphosphino)ferrocene,
1,1'-bis(isopropylcyclohexylphosphino)ferrocene,
1,1'-bis(ditert.butylphosphino)ferrocene,
1-(diisopropylphosphino)-1'-(phenylisopropylphosphino)-ferrocene,
1,1'-bis(di-2-thiophenylphosphino)ferrocene,
1-(diphenylphosphino)-1'-(diisopropylphosphino)ferrocene, and
1,1'-bis(isopropylphenylphosphino)ferrocene.

9. A process according to claim 1, wherein the acid with a $pK_a$ of less than 2 (measured at 18° C. in an aqueous solution) is a fluoro carboxylic acid, $HClO_3$, $H_2SO_4$ or $RSO_3H$, wherein R represents a hydrocarbon group which is an alkyl, aryl, aralkyl or alkaryl group containing 1–30 carbon atoms or a substituted alkyl, aryl, aralkyl or alkaryl group containing 1–30 carbon atoms.

10. A process according to any one of claims 1–4, wherein the alcohol contains 1 to 6 carbon atoms.

11. A process according to any one of claims 1–4, wherein the alcohol is methanol or ethanol.

12. A process according to claim 1, wherein the internally unsaturated organic compound is a substituted or non-substituted alkene with 4 to 20 carbon atoms.

13. A process according to claim 1, wherein the internally unsaturated compound is selected from the group consisting of 2-butene, 2-pentene, 2-hexene, 3-hexene, 2-heptene, 3-heptene, 2-octene, 3-octene, 4-octene, 4-hexene amide, 2-pentenol, 2-butenol, 2-pentenol, 2-pentene nitrile, 3-pentene nitrile, 2-pentenoic methyl ester and 3-pentenoic methyl ester.

14. A process according to claim 1, wherein the internally unsaturated compound is an internally unsaturated alkyl pentenoate having 1 to 8 carbon atoms in the alkyl group.

15. A process according to claim 1, wherein (i) the internally unsaturated compound is methyl pentenoate and the alcohol is methanol, or (ii) the internally unsaturated compound is ethyl pentenoate and the alcohol is ethanol.

16. A process for preparing adipic acid which comprises preparing a dialkyl adipate by carbonylating an internally unsaturated organic compound comprising alkyl 3-pentenoate in the presence of the corresponding alkanol, carbon monoxide, an acid having a $pK_a$ of less than 2 (measured at 18° C. in an aqueous solution) and a bidentate organic phosphorus ligand compound having a bridging group, wherein said bridging group comprises a bis(η-cyclopentadienyl) coordination group of a transition metal; and saponifying said dialkyl adipate to obtain adipic acid.

17. A process according to claim 1, wherein said internally unsaturated compound is an alkene having non-conjugated unsaturated bonds.

18. A process according to claim 1, wherein said internally unsaturated compound in an alkene having one unsaturated bond.

19. A process for the preparation of a terminal ester by carbonylation of at least one pentenoate ester in the presence of an alcohol, carbon monoxide, palladium, an acid with a $pK^a$ of less than 2 (measured at 18° C. in an aqueous solution) and a bidentate organic phosphorus, antimony or arsenic ligand compound having a bridging group, wherein the bridging group comprises a bis(η-cyclopentadienyl) coordination group of a transition metal.

20. A process for the preparation of adipic acid, wherein the ester of adipic acid, which ester is prepared by the process according to claim 19, is saponified to adipic acid.

21. A process according to claim 20, wherein said transition metal is Fe.

22. A process for the preparation of a terminal ester by carbonylation of an internally unsaturated organic compound in the presence of an alcohol, carbon monoxide, palladium, an acid with a $pK^a$ of less than 2 (measured at 18° C. in an aqueous solution) and a bidentate organic phosphorus, antimony or arsenic ligand compound having a bridging group, wherein the bridging group comprises a bis(η-cyclopentadienyl) coordination group of a transition metal wherein the bidentate ligand compound has the following general formula:

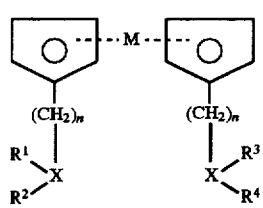
wherein n=0 or 1, X represents a phosphorus, antimony or arsenic atom, M represents Fe and $R^1$, $R^2$, $R^3$ and $R^4$ represent individually an organic group with 1–20 carbon atoms.
* * * * *